United States Patent [19]

Bourguignon et al.

[11] 4,233,245
[45] Nov. 11, 1980

[54] PREPARATION OF TRIS(HYDROXYMETHYL)AMINOMETHANE

[75] Inventors: Jean Bourguignon, Isneauville; Marcel-Xavier Sion, Lewarde; Michel Moreau, Rouen, all of France

[73] Assignee: Societe Chimique de La Grande Paroisse, Azote et Produits Chimiques, Paris, France

[21] Appl. No.: 6,794

[22] Filed: Jan. 25, 1979

[30] Foreign Application Priority Data

Jan. 25, 1978 [FR] France .................................. 78 01965

[51] Int. Cl.$^3$ ............................................. C07C 85/11
[52] U.S. Cl. ...................................... 564/506; 568/712
[58] Field of Search ...................... 260/584 R; 568/712

[56] References Cited

U.S. PATENT DOCUMENTS 2,139,120  12/1938  Hass et al. ............................ 568/712
3,564,062  2/1971  Tindall .................................. 260/635

FOREIGN PATENT DOCUMENTS 1075632  2/1960  Fed. Rep. of Germany ...... 260/584 R
818764  8/1959  United Kingdom ................ 260/584 R Primary Examiner—John Doll
Attorney, Agent, or Firm—Browdy and Neimark

[57] ABSTRACT

Tris(hydroxymethyl)aminomethane, an intermediate of organic synthesis, in crystalline form is made by formylation followed by hydrogenation. Nitromethane and formaldehyde in a molar ratio on the order of 1:3 are reacted in a concentrated alcohol medium made up of a 2 to 5% mixture of methylene chloride in methanol, in the presence of 1 to 10 milliequivalents per mole of nitromethane of a solid base catalyst selected from sodium or potassium, with agitation for a period between 3 and 36 hours at a temperature below 50° C.

6 Claims, No Drawings

PREPARATION OF TRIS(HYDROXYMETHYL)AMINOMETHANE

FIELD OF THE INVENTION

This invention relates to the preparation of tris(hydroxymethyl)aminomethanol in crystalline form.

BACKGROUND OF THE INVENTION

Preparation of nitroalcohol by the action of formaldehyde on nitromethane in a basic medium is known in itself, The basic agent is used in molar proportions or catalytic amounts. The bases are generally alkali or alkaline earth hydroxides, basic ion exchange resins or tertiary amines. All the processes are used in an aqueous or water-alcohol medium. After formylation and elimination of the base, reduction is performed under hydrogen pressure, at times in the presence of carbon dioxide to reduce secondary reactions; there then follow the operations of concentration and crystallization requiring recycling of the recrystallization solvents.

SUMMARY OF THE INVENTION

An improved process has been found that makes it possible to obtain very pure crystallized tris(hydroxymetyl)aminomethane with a yield on the order of 80%, the total yield being greater than 90%.

According to the invention, the tris(hydroxymethy)aminoethane is prepared in a concentrated alcohol medium by the action of polyoxymethylene on nitromethane in the presence of a catalytic amount of a solid alkaline agent and methylene chloride; followed by an acidification and reduction by hydrogen in an alcohol medium containing methylene chloride.

DETAILED DESCRIPTION OF EMBODIMENTS

Nitromethane and formaldehyde in solid form are mixed in a molar ratio on the order of 1:3 in a concentrated alcohol medium made up of a 2 to 5% mixture of methylene chloride in methanol, in the presence of 1 to 10 milliequivalents per mole of nitromethane of a base catalyst in solid form, selected from sodium or potassium, and the reaction proceeds under agitation for a period between 3 and 36 hours at a temperature below 50° C.

The product formed in the formylation phase is acidified by a concentrated acid to a pH between 2.7 and 7, preferably between 4.5 and 5.5. The nitroalcohol thus obtained is diluted in methanol containing 2 to 5% methylene chloride, preferably 2.5%; it is then hydrogenated with hydrogen to the exclusion of any other gaseous constituent under a hydrogen pressure between 30 and 60 bars, in the presence of Raney nickel. The amount of hydrogenation catalyst is selected so that it represents 5 to 25% by weight of the nitroalcohol to be reduced.

After hydrogenation, the reaction medium is filtered to eliminate the catalyst, and is cooled to 0° C. The yield in the first batch of tris(hydroxymethyl)aminomethane of great purity, separated directly by cooling of the reaction medium, amounts to 60–65%. By concentration of the mother liquors to an oily residue which is taken up by a 30% mixture of methanol in methylene chloride, a second batch of tris(hydroxymethyl)aminomethane is isolated with a purity identical with that of the first batch, bringing the total yield to 75–80%. A third crystallization makes it possible to recover a last batch of acceptable quality, with a yield that the total yield such is above 90%.

An example that illustrates the invention in a nonlimiting way is given below.

EXAMPLE

To 0.331 mole of nitromethane in 35 ml of methanol containing 1 ml of methylene chloride, there is added, with agitation of sodium in pellet form in such an amount that the pH is kept between 8 and 9, polyoxymethylene corresponding to 0.933 mole of formaldehyde. During the reaction of 2 hours with agitation of the reaction mixture, the temperature is maintained between 45° and 55° C.

When all the formaldehyde added has been consumed by the reaction, the pH is lowered to 4.5 by addition of concentrated hydrochloric acid.

The resulting nitroalcohol is introduced dilute into 250 ml of methanol and 2 ml of methylene chloride in hydrogenation reactor. The mixture is hydrogenated on Raney nickel, representing 5% by weight of the nitroalcohol to be reduced, under a pressure of 30 bars at a temperature of 40° C. to 47° C.

After absorption of the hydrogen has been completed, the catalyst is separated by filtration, and washed with 90 ml of methanol with 2% methylene chloride. The washing methanol is added to the reaction product.

The reaction product is cooled in a methanol medium for two hours at 0° C. By crystallization, tris(hyroxymethyl)aminomethane is obtained with a molar yield of 62% having a melting point of 170° C. with a purity greater than 99.5% found by acidimetric determination. Microanalysis of this product is correct, i.e., the percentages of C, H and N found do not differ by more than 0.2% in absolute value from the theoretical value.

The first crystallization mother liquors are evaporated, and the oil residue is picked up with a mixture of 5 ml of methanol and 10 ml of methylene chloride. After cooling, crystals are obtained which are washed with the methanol-methylene chloride mixture, then in methanol; the total yield of the first and second crystallization is 77.6% tris(hydroxymethyl)aminomethane with a melting point of 169° C., with a purity of 98& by acidimetry. The microanalysis is still correct. A third crystallization makes it possible to recover an additional amount of tris(hydroxymethyl)aminomethane with a purity close to 93% determined by acidimetry, with a melting point of 165° C., and bringing the total yield to more than 90%.

What is claimed is:

1. in a process of preparing tris(hydroxymethyl)aminomethane in crystalline form separated directly by cooling of the reaction medium, the process comprising formylation followed by hydrogenation, the improvement wherein nitromethane and formaldehyde, in polyoxymethylene or solid form, are reacted to effect said formylation in a molar ratio on the order of 1:3 in a concentrated alcohol medium of 2 to 5% mixture of methylene chloride in methanol, in the presence of 1 to 10 milliequivalents per mole of nitromethane of a basic catalyst in solid form, selected from sodium or potassium, with agitation for a period between 2 and 36 hours at a temperature below 55° C.; and the product of the formylation is acidified with concentrated acid to a pH between 4.5 and 5.5, the resultant acidified nitroalcohol is diluted with methanol containing 2 to 5% methylene chloride, and is then catalytically hydrogenated on Raney nickel at a hydrogen pressure of 30 to 60 bars at a temperature of 40 to 47° C.

2. Process of preparing tris(hydroxymethyl)aminomethane according to claim 1 wherein the weight of the Raney nickel is between 5 and 25% in relation to the weight of the nitroalcohol to be reduced.

3. Process of preparing tris(hydroxymethyl)aminomethane accordance to claim 1 wherein the dilution methanol contains 2.5% methylene chloride.

4. In a process of preparing tris (hydroxymethyl) aminomethane in crystalline form separated directly by cooling of the reaction medium, by formylation followed by hydrogenation, the improvement comprising formylating nitromethane by reaction with formaldehyde, in polyoxymethylene or solid form, in concentrated methanol containing 2–5% methylene chloride, in the presence of 1 to 10 milliequivalents of sodium in solid form per mole of nitromethane, the mole ratio of nitromethane to formaldehyde being on the order of 1:3; acidifying the resultant product of the formylation reaction with concentrated hydrochloric acid to a pH between 4.5 and 5.5, diluting the resultant acidified nitroalcohol with methanol containing 2 to 5% methylene chloride, and then catalytically hydrogenating using Raney nickel at a hydrogen pressure between 30 and 60 bars and a temperature between 40° and 47° C., whereby tris(hydroxymethyl)aminomethane is precipitated in crystalline form.

5. Process in accordance with claim 4, wherein the weight of the Raney nickel is between 5 and 25% in relation to the weight of the nitroalcohol to be reduced.

6. Process in accordance with claim 4, wherein the dilution methanol contains 2.5% methylene chloride.

7. Process of preparing tris(hydroxymethyl)aminoethane according to any of claims 1 to 6 wherein a first batch of the final product in crystalline form is separated directly by cooling of the reaction medium free of hydrogenation catalyst; then a second batch, of generally the same purity as the first, is obtained after separation of the first batch followed by concentration of the mother liquors to an oily residue and extraction from the oily residue by a 30% mixture of methanol in methylene chloride.

* * * * *

UNITED STATES PATENT AND TRADEMARK OFFICE
CERTIFICATE OF CORRECTION

PATENT NO. : 4,233,245
DATED : November 11, 1980
INVENTOR(S) : BOURGUIGNON et al It is certified that error appears in the above-identified patent and that said Letters Patent are hereby corrected as shown below:

Abstract, line 9, after "sodium" and after "potassium" insert --hydroxide--
Column 1, line 43, after "sodium" insert --hydroxide--
    lines 43-44, after "potassium" insert --hydroxide--
Column 2, line 9, after "sodium" insert --hydroxide--
Claim 1, line 11, after "sodium" insert --hydroxide--
    lines 11-12, after "potassium" insert --hydroxide--
Claim 4, line 8, after "sodium" insert --hydroxide--

Signed and Sealed this

Twenty-first Day of July 1981

[SEAL]

Attest:

Attesting Officer

GERALD J. MOSSINGHOFF

Commissioner of Patents and Trademarks